United States Patent [19]

Stirnadel

[11] Plant 4,761

[45] Aug. 25, 1981

[54] EUPHORBIA PLANT

[76] Inventor: Alfred Stirnadel, Schwarzwaldstr. 80, 6660 Zweibrücken 15, Fed. Rep. of Germany

[21] Appl. No.: 85,426

[22] Filed: Oct. 16, 1979

[30] Foreign Application Priority Data

Oct. 28, 1978 [DE] Fed. Rep. of Germany ..... 2845840

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—William H. Elliott, Jr.

[57] ABSTRACT

A new variety of Euphorbia plant, being an asexually-reproduced hybrid of *Euphorbia lophogona* and *Euphorbia milii* which produces flowers in biaxial ramification, the clusters of which are up to about 15 cm in length, the flowers being yellowish in color and the bracts being up to 32 in number and from salmon pink to luminous salmon red in color, the plant being further characterized by an "ever-blooming" quality, under suitable environmental conditions. Propagation of this new variety is enhanced by control of environment to provide 1000 lux artificial light for a 12½-hour day at temperatures from 22°–25° C. and humidity 60–90 percent.

1 Drawing Figure

This invention relates to a salmon-colored Euphorbia hybrid and method of vegetative propagation.

The objective of the invention is the production of a uniform Euphorbia hybrid with stable new characteristics, pertaining to a new plant variety of the Euphorbia genus, as well as method of vegetative propagation through production of shoots.

In 1970 applicant found (among many thousand Euphorbia plants growing in a cultivated state in the garden of a Catholic mission in Fort Dauphin, Madagascar where a program of controlled breeding was being carried out) an especially striking Euphorbia hybrid with particularly abundant blossoms of luminous salmon-red color which he brought back to develop a marketable container plant for the garden trade. The test results showed that this Euphorbia hybrid was the result of crossbreeding between *Euphorbia lophogona,* as the mother plant, and *Euphorbia milii,* as the father plant.

The applicant has developed, as described hereinafter, a new method of vegetative propagation through shoot production from the original plant of the new Euphorbia variety and has thus built up a mother-plant stock; from this and pre- and post-selection based on scientific selection studies, he finally produced a new Euphorbia variety, more precisely described hereinafter, which in addition to the novel propagation method is the objective of this patent application.

Since the original plant, with a lifespan of many years duration, does not produce shoots under middle European climatic conditions and temperature range, the applicant undertook numerous experiments whereby he exposed the plant to various conditions of artificial light irradiation at various temperatures and particularly at various degrees of humidity. These tests finally resulted in shoots being produced by the original plant under the following conditions:

The plants were exposed to an average light intensity of 1000 lux by exposure to artificial light or shade for a 12½-hour day. They were kept at a temperature of 22°–25° C. and a humidity of 60–90 percent throughout the experiment.

The applicant thus discovered a new method permitting said Euphorbia hybrid to propagate under European climatic conditions, something that was impossible before the advent of this new method. This method can also be used on other varieties of this species. In any case, this method can be used on all Euphorbia varieties which could not be propagated in middle Europe under normal conditions. In addition, the invention contemplates that other varieties of Euphorbia plants which could not be propagated under middle European conditions can be propagated by altering the light conditions necessary for vegetative propagation.

The characteristics and properties of the new Euphorbia variety can be reproduced fully at anytime by using the aforementioned method of vegetative propagation through production of shoots, however, naturally occurring variations resulting from differences in environment have to be allowed for.

The new Euphorbia variety produced by the aforementioned method, as well as the method of vegetative propagation, are placed under protection.

The individual characteristics of the new Euphorbia variety are summarized below; and in the following description the color descriptions preceded by the initials "RHS-" refer to Royal Horticultural Society Colour Chart color designations:

Plant: The plant grows in an upright slightly bushy habit, i.e., with ascending branches in the lower regions of the main stem; and produces blossoms after reaching a height of about 10 cm. Under appropriate conditions, a new blossom cluster is produced with each leaf approximately every 10–14 days. If the plant is not pruned, it will grow approximately 10–12 cm. per year.

Stem: The stem is grey-green in color, slightly succulent, 1 to 1.5 cm in diameter, with 4 to 5 ridges on which small nodes occur at 2 cm intervals, bearing up to 10 red-brown thorns 0.5 to 2 cm in length. Thus the stem is of a generally pentagonal cross-section through the thorn cluster.

Leaves: The alternately arranged leaves extend almost horizontally outward from the stem and branches. The leaves have a short stalk. Ramification from the leaf axis is possible. The leaves are slightly pulpy, dark green (RHS-139A) on the upper side and light green (between RHS-139C and RHS-139D) on the underside; they are of varying length and width up to about 15 cm in length and up to about 5 cm in width and usually about 3–4 cm in width. The leaves are spatulate, with tips varying from very slightly emarginate to very slightly mucronate and an acuminate base. The leaves have a thick middle vein, and short stalk. The thorn clusters are located on nodes on both sides of the leaf axis. A white milky sap exudes from all plant parts when subjected to injury.

Blossoms: A blossom cluster consists of up to 32 single blossoms (each having two salmon-pink to luminous salmon-red bracts) on one pedicle with multiple ramification. Usually, the upper side of the bracts are bluish carmine (RHS-52A) and the underside of the bracts are carmine rose (RHS-52D). Discoloration is slight upon light variation. New blossom clusters arise from each new leaf axis on light green stalks up to 3 mm in thickness and up to about 15 cm in length but usually 5 to 8 cm in length. Each blossom cluster is of layered configuration since, as a rule, two new blossoms develop from each individual blossom (biaxial ramification). The bracts of an individual blossom surround the flower organs and are rounded off, slightly superposed, with a central indentation and slightly sinous on both sides; they achieve a width of up to 15 mm. In the appropriate environment, the plant will bloom uninterruptedly. Depending on the temperature and light conditions, the sapling stage of the single blossom has a duration of 8–14 days from the closed flower-bud to the opening of the bracts (false blossoms) and the subsequent appearance of the female ovary. The individual blossom is yellowish and dull; the three-part female ovary that appears during the sapling stage, and after 2–4 days, the pollinatable ovary withdraws and the male blossom organs (stamens) appear. The male stamen grows up to 4 mm in height.

The accompanying drawing shows, in color, a plant of the new Euphorbia variety in full bloom.

I claim:

1. A hybrid plant of the genus Euphorbia, substantially as herein shown and described and particularly characterized in that it is the result of crossbreeding between a plant of the *Euphorbia lophogona* species, as the mother plant, and a plant of the *Euphorbia milii* species, as the father plant, and exhibits the following characteristics: succulent stem with 4 to 5 ridges on which small nodes occur at 2 cm intervals bearing up to 10 red-brown thorns 2 cm in length; blossom clusters up to 15 cm in length form at each new leaf axis and bear up to 32 single blossoms each having two salmon pink to luminous salmon red bracts on light green stalks up to 3 mm in thickness; layered configuration of each blossom cluster whereby, as a rule, two new blossoms develop from each single blossom; the alternately arranged spatulate leaves are slightly pulpy, about 15 cm in length and up to 5 cm in width with a short stalk, said plant being further characterized in that, in the appropriate environment, the plant will bloom uninterruptedly.

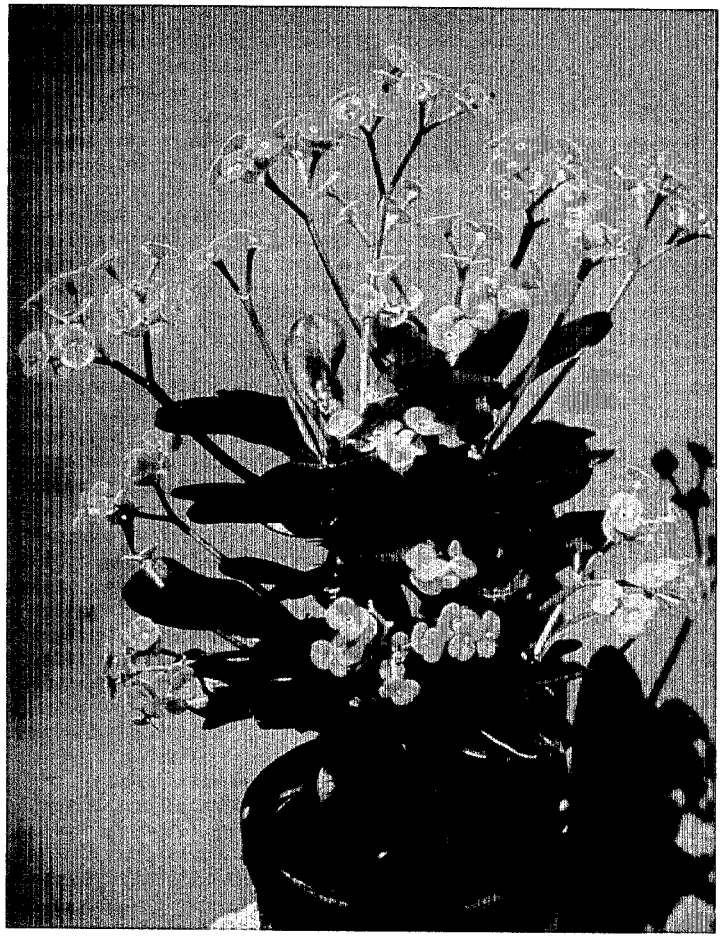

* * * * *